United States Patent
Johnson (10) Patent No.: US 7,238,021 B1
(45) Date of Patent: Jul. 3, 2007

(54) POWERED CUTTING SURFACE WITH PROTECTIVE GUARD FOR EQUINE TEETH

(76) Inventor: Gary E. Johnson, 22711 Western Ave., Torrance, CA (US) 90501-4994

( * ) Notice: Subject to any disclaimer, the term of this patent is extended or adjusted under 35 U.S.C. 154(b) by 0 days.

(21) Appl. No.: 09/204,866

(22) Filed: Dec. 3, 1998

(51) Int. Cl.
- A61D 5/00 (2006.01)
- A61C 1/16 (2006.01)
- A61C 1/18 (2006.01)

(52) U.S. Cl. ............................. 433/1; 433/112; 433/116
(58) Field of Classification Search ................... 433/1, 433/105, 112, 116
See application file for complete search history.

(56) References Cited

U.S. PATENT DOCUMENTS

| | | | | |
|---|---|---|---|---|
| 614,829 | A | * | 11/1898 | Brown ........................ 433/105 |
| 2,429,356 | A | * | 10/1947 | Hicks .......................... 433/116 |
| 4,722,685 | A | * | 2/1988 | de Estrada .................... 433/1 |
| 5,964,590 | A | * | 10/1999 | Loddeke et al. ............. 433/126 |

FOREIGN PATENT DOCUMENTS

SE  110103  *  3/1944  .................... 433/1

* cited by examiner

Primary Examiner—John J Wilson

(74) Attorney, Agent, or Firm—John E. Halamka

(57) ABSTRACT

An arrangement that may be used in combination with selected tools having a tooth cutting surface for the care and maintenance such as removing a selected portion of the exposed surface of equine teeth. The selected tool in communication with a source of powered motion and mounted in and supported by a hand piece which is guided into the mouth of the horse. The cutting surface of the powered tool is partially guarded so as to protect fleshy portions of the horse's mouth from being engaged by the cutting surface. The hand piece provides for quick on and off attachment of a selected cutting surface for maintenance of a preselected portion of teeth within the same hand piece or another hand piece sized to ease access to the next selected portion of the horse's mouth. The selected hand piece arrangement may further incorporate a vacuum channel whereby the tooth dust and debris created by the powered cutting surface removing a portion of tooth is sucked out of the mouth of the horse. The motion of the tooth surface removal tool may be changed from rotary to powered reciprocating motion for a selected portion of the teeth or changed to be at a preselected angle. Attaching the powered drive to the rotary cutting surface by means of an adjustable clutch further enhances protection from injury to the inside of the mouth of the horse.

20 Claims, 11 Drawing Sheets

POWERED CUTTING SURFACE WITH PROTECTIVE GUARD FOR EQUINE TEETH

BACKGROUND OF THE INVENTION

1. Field of the Invention

This invention relates to the art of tooth maintenance for large animals and more particularly to a set of tools which may be used under powered motion for care and maintenance such as removing a selected portion of the exposed surface of teeth, such as equine teeth, with the powered hand being guided into the mouth of the horse. The powered tool is partially guarded so as to protect fleshy portions of the horse's mouth from being engaged by the powered tool. The tool may have a rotary cutting surface of a selected size and shape, sometimes commonly called a burr, or the tool may be a rotary cut-off disk. The selected tool, either the burr or cut-off disk, is supported and partially enclosed in a protective guard formed as a hand piece that may be guided into the mouth of a horse to perform care and maintenance on a selected portion of the teeth. The hand piece fabricated according to the teaching of this invention provides for quick on and off attachment of a selected cutting surface for maintenance of a preselected portion of teeth within the same hand piece or another hand piece sized to ease access to the next selected portion of the horse's mouth. The selected cutting surface is mounted within the protective guard/hand piece arrangement that may further incorporate a vacuum channel whereby the tooth dust and debris created by the powered cutting surface removing a portion of tooth is sucked out of the mouth of the horse. The motion of the tooth surface removal tool may be changed from rotary to powered reciprocating motion for a selected portion of the teeth. Attaching the powered drive to the rotary cutting surface by means of an adjustable clutch further enhances protection from injury to the inside of the mouth of the horse.

2. Description of the Prior Art

Throughout the life of the horse, the teeth continue to extend from the gums. When non-domesticated horses graze on the ground, they pick up sand and hard particles in the grass, which would naturally reduce the growth of the horse's teeth.

In order for domesticated horses to properly chew their food, which consists mostly of preprocessed grain and formula, the teeth require periodic maintenance. Without the natural wearing of the teeth from grazing on the ground, the teeth may grow uneven and too long, thus interfering with normal eating.

In the past, regular dental care to remove points, hooks or ridges that have grown or worn into the teeth required the use of a specially designed rasp-like tool to remove them, a process called floating the teeth. Because of the structure of the teeth, the horse does not have nerves extending upward in the teeth and therefore feels no pain when the teeth are filed to reshape them.

A grown horse uses 36 teeth to eat. The 6 upper incisors and the 6 lower incisors are for shearing grass and leaves, which are masticated by 12 premolars, and 12 molars located on both sides of the upper and lower jaws. These molars must align for the horse to chew properly.

The majority of dental problems are associated with the molars and premolars. However, if the incisors are to long, opposing molars and premolars may be prevented from engaging properly.

In the prior art, hand tools similar to metal files or rasps were used to remove a selected portion of the tooth surface. These tools consisted of several shaped handles with pads mounted on one end. The pads accepted plates having an abrasive or specially designed file or rasp-toothed surface selected by the user. The mounted abrasive or rasp on the handle was then inserted into the horse's mouth and positioned against the tooth structure that needed to be altered. The user then manually applied pressure and movement to the handle until the selected portion of the tooth structure was removed.

Some prior solutions to the problem were to add motor power to the burrs to provide a "power dental tool" to replace the manual rasps. These solutions ease the manual work but introduced other problems such as the uncontrolled creation of dust and debris as well as the danger of injury to the horse and user from exposed high speed reciprocating or rotary burrs or rasps which may engage soft tissue such as the cheek, tongue, or gums inside the horses mouth.

Thus, there has long been a need for an arrangement that allows the user, usually a veterinarian, an owner or an equine dentist, to easily perform the removal of preselected material from the exposed surface of the horse's teeth without danger to the horse or the person doing the job.

It is desired that the arrangement allow the user to access the full array of teeth with a set of preselected shaped and surfaced files, rasps or other tools such as diamond cut-off blades.

It is further desired that the arrangement be motor driven but provide safety to the user and horse.

It is further desired to provide preselected shaped covers or guards around selected portions of the rotary tool to allow the system to be used in all parts of the mouth of the horse.

It is further desired to provide a clutch between the motor and the rotary tool. The threshold of disengagement of the rotary power applied by means of the clutch may be adjustable with access for adjustment that does not require dismantling the system.

It is further desired that the arrangement be able to remove accumulation of debris from the inside of the horse's mouth during the procedure.

It is desired that a simple latching or unlatching movement engage and disengage the selected tool within the rotary driven arrangement.

It is desired that a simple latching or unlatching movement engage and disengage selected guards around the rotary tool.

It is further desired that during the operation of the arrangement for the removal of material from inside the mouth the inadvertent engagement of soft tissue inside the mouth not adversely affect the user or the horse.

It is desired that reconfiguration of the arrangement be accomplished even if the users hands are slippery.

It is further desired that the motor be separated from the rotary tool by a drive train so that the user need not support the weight of the motor during the procedure.

It is further desired that the arrangement be easily adapted to a "power dental tool" motor or handle the user may presently own.

SUMMARY OF THE INVENTION

Accordingly, it is an object of the present invention to provide an arrangement that allows the user to safely and easily perform a dental procedure of removal of preselected material from the exposed surface of the teeth of horses.

It is another object of the present invention to provide an array of preselected size, shape and surfaced tools to be used to remove the tooth material as well as a means for quickly changing the rotary tool selected and provide a guard around a selected portion of the rotary tool so that it does not engage the flesh inside the mouth of the horse.

It is an object of the present invention to provide a clutch arrangement which allows the user to initially adjust the threshold at which the rotary motion will disengage should the rotary tool inadvertently entangle flesh inside the mouth of the horse. It is a further object that said threshold may be easily changed as the procedure progresses among various portions of the mouth without dismantling the system.

It is another object of the present invention to provide a method of removal of the tooth material debris from inside of mouth of the horse without stopping or interfering with the progress of the procedure.

It is yet another object of the present invention to provide an arrangement which does not require the user to support the motor during the procedure.

It is yet another object of the present invention to be easily mountable on or at least partially adapted to a "power dental tool" which may be currently owned by the user.

The above and other objects of the present invention are achieved, according to a preferred embodiment thereof, by providing a system of an improved power tool arrangement of a motor, power train, tools that remove tooth material, rotary tool hand pieces which support the tools for rotary motion or reciprocating motion and provide a guard to separate the tool from soft tissue. The arrangement is provided with means to easily reconfigure the tool, tool support and guard to adapt the system for powered removal of preselected portions of teeth.

Motor

The power for the preferred arrangement may be supplied from a preselected off the shelf rotary hand tool that may be obtained in various configurations of torque and adjustable rpm under the trademarks DREMEL or SUHNER. Each motor is designed to accept the shaft of a tool with an arrangement of a collet. The tool may have a selected cutting surface and a selected length of shaft. The rotary hand tool may be enhanced with a flexible shaft, one end adaptively mountable on the rotating shaft of the motor and the remote end attachable to an optional handle whereby under the condition of the rotary tool being mounted on the handle, the user may perform work by directing the rotary tool remote from the motor without having to support the weight of the motor. The motor may be supported within a backpack, fannypack or sling arrangement worn by the user.

Power Train

The flexible shaft that may be mounted between the motor and the tool removes the burden of holding the motor and physically separates the motor from the tool thereby diminishing the level of sound of the arrangement that may be disturbing to the horse. One end of the flexible shaft may incorporate an adapter for quick push on connection with the selected motor, the end attachable to the hand piece may be fabricated with a stainless steel sleeve and shaped to incorporate a catch engagable with a latch mounted on the hand piece. The length of the flexible shaft may be selected to provide easy movement of the end of the shaft remote from the motor.

However, the flexible shaft arrangements provide direct coupling between the motor and the rotary tool. Should the tool engage a portion of the soft flesh inside the mouth of the horse or bind against the surface of the teeth, the rotational energy of this direct connection may cause damage to the horse before the tool can be removed or the power disconnected from the motor. In the present invention an adapter is provided between the motor and the flexible shaft. An adjustable clutch is mounted within the adapter to be accessible to the user to adjust the threshold of torque transmitted between the motor and the flexible shaft of the power train. Should the tool bind, as soon as the selected threshold is exceeded, the movement of the power train is interrupted so that the user may safely disengage the tool or clear the obstruction thereby providing protection to the horse and user of the arrangement.

Tool

It is possible to obtain off the shelf tools to which rotary motion is applied. The tool is mountable in the motor and generally consists of a shaft and a working surface mounted on the end of the shaft. The shaft is nominally no longer than 1 to 2½ inches. The working surface is provided in an array of shapes, sizes and surfaces. Some of the preferred shapes include a sphere, cone, cylinder, and combinations such as cylinder topped by a half sphere. These tools may be commonly called a burr. The cutting surface formed in the tool may be a preselected pattern of raised rasp like teeth of a preselected size and shape which removes tooth material without binding, bouncing or filling the rasp like teeth with debris.

Another type of rotary tool is the cut-off disk which is a platter about the size of a quarter covered with diamond dust and mounted on a shaft. This disk may be used edge on to cut off a selected portion of a tooth rather than grind off the portion with a burr. The edge of the disk may also be used to score the selected portion of tooth so that portion may be chipped off. The flat surface of the disk may be used as a polishing tool or may be used to round off any sharp edges like a disk sander.

If a tool having a working surface is mounted within a collet either on the end of the motor or on the end of the handle attached to the motor or end of a flexible drive shaft and the rotary tool has a shaft length of more than approximately 2½ inches, the operation of this configuration of an extended cutting surface rotating at high speed and fully exposed, may be dangerous to the user and to the work piece, in this case the mouth of a horse. The mouth of a horse is deep and requires a tool of at least 12 inches in length to adequately reach the exposed surface of the back molars.

Guard and Rotory Tool Support

A guard in the form of an encircling shield may be installed around the tool's shaft and cutting surface to separate the user and portions of the horse's mouth from the tool which is in rotary motion. The guard should be fabricated to have a minimal opening to allow only a selected portion of the cutting surface to be exposed. The hand piece, mountable on the end of the motor or flexible shaft, may be fabricated to incorporate the guard in a manner that allows the tool to be mounted within a channel of the hand piece thereby supporting the shaft and encircling the cutting surface. Support of the shaft is generally required if the shaft of the tool is longer than approximately 4 inches in order to reach into all areas of the mouth of the horse, pressing the cutting surface onto the surface of the tooth may move the shaft and or cutting surface against the safety shield or channel of the handpiece. Bearings may be mounted at preselected positions along the channel to support and protect the rotating shaft and cutting surface under conditions of engaging the channel or guard surfaces.

The hand piece may be supplied as a set of selected lengths specially adapted to service a selected portion of the horse's mouth. A 6 to 8 inch hand piece may be used to service the incisors. A 12 to 14 inch handpiece may be used for the back molars. An 8 to 12 hand piece may be supplied for intermediate service whereas a 10-inch hand piece is the recommended length for an all around arrangement.

The hand piece may include a second channel partially separate from the rotary tool channel. The hand piece may be fabricated to form an orifice near the cutting surface whereby the orifice is in communication with the second channel. The end of the second channel remote from the cutting surface is attachable to a vacuum source such as a "SHOP VAC"® whereby tooth material removed by the cutting surface may be sucked out of the mouth of the horse along the second channel without having to remove the hand piece from the mouth of the horse.

The hand piece may also incorporate appropriate gearing and joints to transpose the rotary motion of the motor and apply a reciprocating motion to the tool mounted on hand piece. The reciprocating tool usually contains a textured surface to remove tooth material especially from the rear most molars which so abuts the gum of the horse that the use of a rotating tool even with a guard may cause injury to the gum.

In the preferred embodiment, the incorporation of an adjustable clutch within the power train, mounting of at least one support bearing within the handpiece, mounting the rotary tool with a guard and further providing for the mounting of shaped guard extensions on the surface of the guard provides a quick reconfiguration of the arrangement during the procedure that provides care and maintenance for the entire set of teeth.

An adapter may be provided to allow the user to use at least a portion of the arrangement such as the tool handpiece and guard system with a power dental device already owned by the user.

BRIEF DESCRIPTION OF THE DRAWINGS

The above and other embodiments of the present invention may be more fully understood from the following detailed description, taken together with the accompanying drawings, wherein similar reference characters refer to similar elements throughout, and in which:

FIG. 1A, B, C, D and E are front views of the present invention;

FIG. 4 A, B, C, and D are views and a cross section of the present invention;

FIG. 5 A, B, and C are views of another embodiment of the present invention;

FIG. 6 B and F are views of another embodiment of the present invention, FIG. 6 H is a view of the hose;

FIG. 7 B and F are views of a flange;

FIG. 8 is a cross sectional view of the present invention;

FIG. 9 is a cross sectional view of the present invention;

FIG. 10 is a front view of the bearing support;

FIG. 12 X, Y and Z and A, B, C are views of another embodiment of the present invention;

DESCRIPTION OF A PREFERRED EMBODIMENT

Referring now to the drawing, there is illustrated in FIGS. 1A through 1E an embodiment of an arrangement fabricated according to the teaching of the present invention and generally designated 10. FIG. 1A illustrates a rotary tool support generally designated 301 mountable within a hand piece generally designated 401. The hand piece 401 is fabricated to form a guard around a selected portion of the cutting surface 302. This embodiment is adapted to be attachable to a motor directly or by means of a flexible shaft and/or a handle that the user may own.

The rotary tool support 301 illustrated in FIG. 1A is fabricated to support the shaft 303 of the rotary tool with a cutting surface 302 mounted on the shaft 303, even if a long shaft 303 (greater than 6 inches) is used.

Now referring to FIG. 1C, the hand piece 401 fabricated according to the principals of the present invention incorporates the base 403 which may be fabricated to adapt the arrangement to a powered rotating source, such as a flexible shaft which is engable with the shaft 303, or be mountable directly on the end of a powered rotating source already owned by the user. The end of the hand piece 401 remote from the powered rotating source is fabricated as a guard encircling a selected portion of the cutting surface 302 and may accept the mounting of an extended guard 406. The long shaft 303 of the rotary tool is required so that the arrangement may be used to reach even the rear most teeth within the mouth of the horse. The shape of the extended guard 406 may be selected to protect a particular portion of the horse's mouth and thus may form a set of removable attachable guards.

Figure 1:
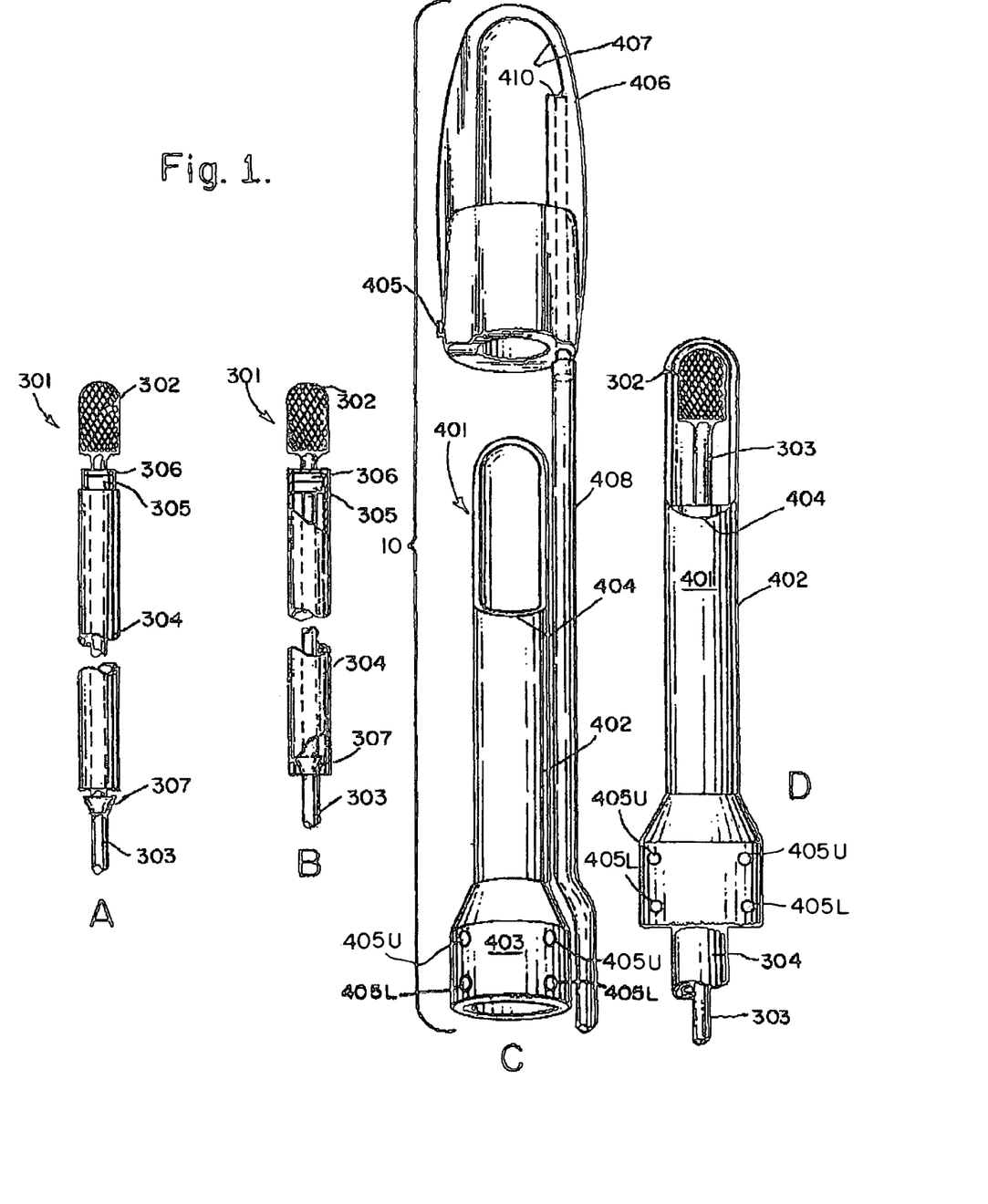

Now referring to FIG. 1 A, there is illustrated a rotary tool support generally designated 301. The rotary tool mounted with the support 301 has a cutting surface 302 mounted on a shaft 303, this illustrated combination is commonly known as a burr. The shaft 303 extends along a bearing support sleeve 304. In the preferred embodiment, a bearing 305 is press fit into the end of the sleeve 304 nearest the cutting surface 302. An upper shaft seal 306 is mounted above the bearing 305. A lower shaft seal 307 may be mounted on the end of the shaft 303 remote from the cutting surface 302 to protect the bearing 305 from contamination. FIG. 1 B shows the rotary tool support 301 fully assembled.

FIG. 1 C illustrates a hand piece generally designated 401. An outer shell fabricated of a capped tube 402 is mounted into an adaptive base 403 having a plurality of setscrews 405 depicted as an upper pair 405U and a lower pair 405L. The diameter of the tube 402 is selected to be a snug fit for the fully assembled rotary tool support 301 but allow the tool support 301 to be easily inserted into or removed from the tube 402. A selected upper portion of the tube 402 is removed down to the lower edge 404 to form an opening and expose a selected portion of the cutting surface 302. The remainder of the outer shell capped tube 402 forms a shield around the cutting surface 302. If more protection is desired an external guard 406 of preselected shape may be slid over the end of the tube 402 and secured in place with a set screw 405. The shape of the external guard 406 is selected so as to not come into contact with the cutting surface 302. Walls 407 form an opening in the external guard 406 to expose a preselected portion of the cutting surface 302.

Figure 1E:
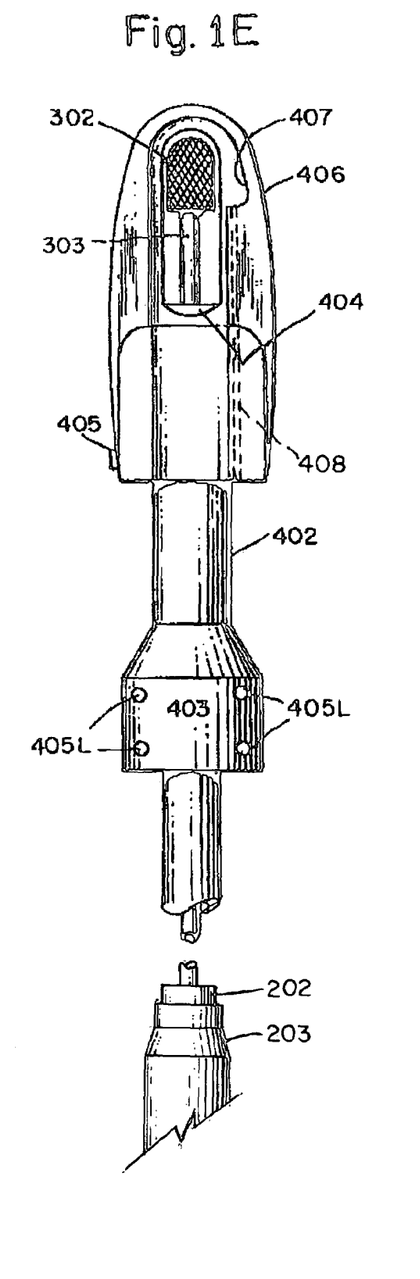

FIG. 1 D illustrates the rotary tool support 301 fully inserted into the hand piece 401 and secured lightly therein by the upper pair of setscrews 405U. The end of the shaft 303 remote from the cutting surface 302 is mounted into the collet 202. In this embodiment, the collet 202 is mounted on the end of a flexible shaft handle 203, which may be mounted to a motor. The adaptive base 403 is installed over the flexible shaft handle 203 and tightly secured in place by the lower pair of setscrews 405L followed by tightening the upper pair of set screws 405U. FIG. 1 E shows the exposed portion of the cutting surface 302 surrounded by the hand piece 401 and external guard 406 fully assembled.

The external guard 406 may be fabricated with second wall 409 forming an intake orifice 410 at a preselected position near the cutting surface 302. A vacuum channel 408, which in the preferred embodiment is a hollow tube, may be mounted or fabricated within the external guard 406, positioned essentially parallel to the handpiece 401 and in communication with the orifice 410. As the channel 408 has one end making a connection with the intake orifice 401 formed by second wall 409, the channel 408 provides an open passage way for sucking out dust and debris created during use of the cutting surface 302 upon the condition of a vacuum source attached to the end of channel 408 remote from the intake orifice 410.

Figure 2:
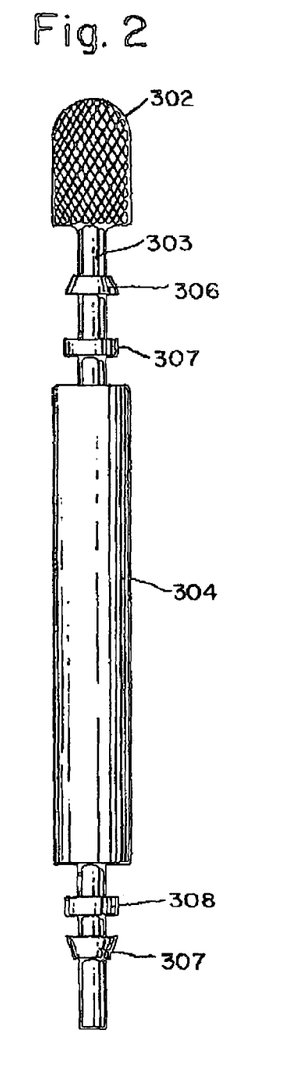
FIG. 2 is a front view of a bearing support.

In FIG. 2 there is illustrated another embodiment of the rotary tool support 301 fabricated as above with the addition of a lower bearing 308 mounted within the bearing support sleeve 304 above the lower shaft seal 307. However, when the shaft 303 in such a multiple bearing arrangement is mounted within the collet 202 of the flexible shaft handle 203, should the flexible shaft handle 203 also be fabricated with a multiple bearing arrangement, a misalignment of the bearings of the flexible shaft handle 203 and the bearings supporting shaft 303 may occur to cause excessive wear on one or more of the bearings or may cause the arrangement to bind and not be smoothly rotatable by the motor. This binding may be overcome by providing a means to adjust the alignment of the bearings.

If the lower bearing 308 and external seal 307 are removed to overcome any binding problem then another problem may develop. During use of the arrangement, the end of the bearing support sleeve 304 remote from the cutting surface 302 may come into contact with the collet 202 causing excessive wear to the point that the collet 202 cannot be loosened for the removal of the shaft 303.

Figure 3:
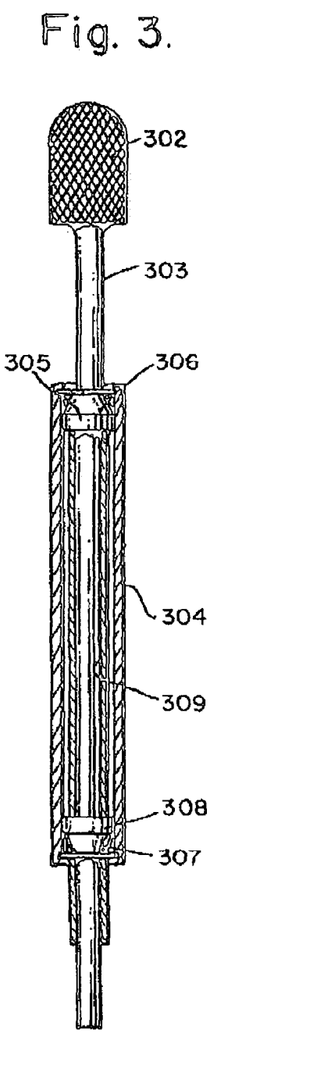
FIG. 3 is a front view of another bearing support.

FIG. 3 illustrates a solution. The use of a lower bearing 308 and lower seal 307 can be eliminated and damage to the collet 202 be avoided by mounting a hollow brass tube 309 onto the shaft 303. Upon the mounting of the shaft 303 into the collet 202, the end of the brass tube 309 may be positioned to be spaced apart form the collet 202 or in contact with the collet 202. However the end of the sleeve 304 should not be in contact with the collet 202. The brass tube 309 extends from below the upper bearing 305 to a selected distance, 1/16 to 1/8 inch, below the end of the bearing support sleeve 304 remote from the upper bearing 305. Upon use of this arrangement, the brass tube 309 performs the function of a bearing by allowing the remote end of the sleeve 304 to come into contact with the brass tube 309 but the brass tube 309 keeps the sleeve 304 separate and apart from the rotating shaft 303.

Figure 4:
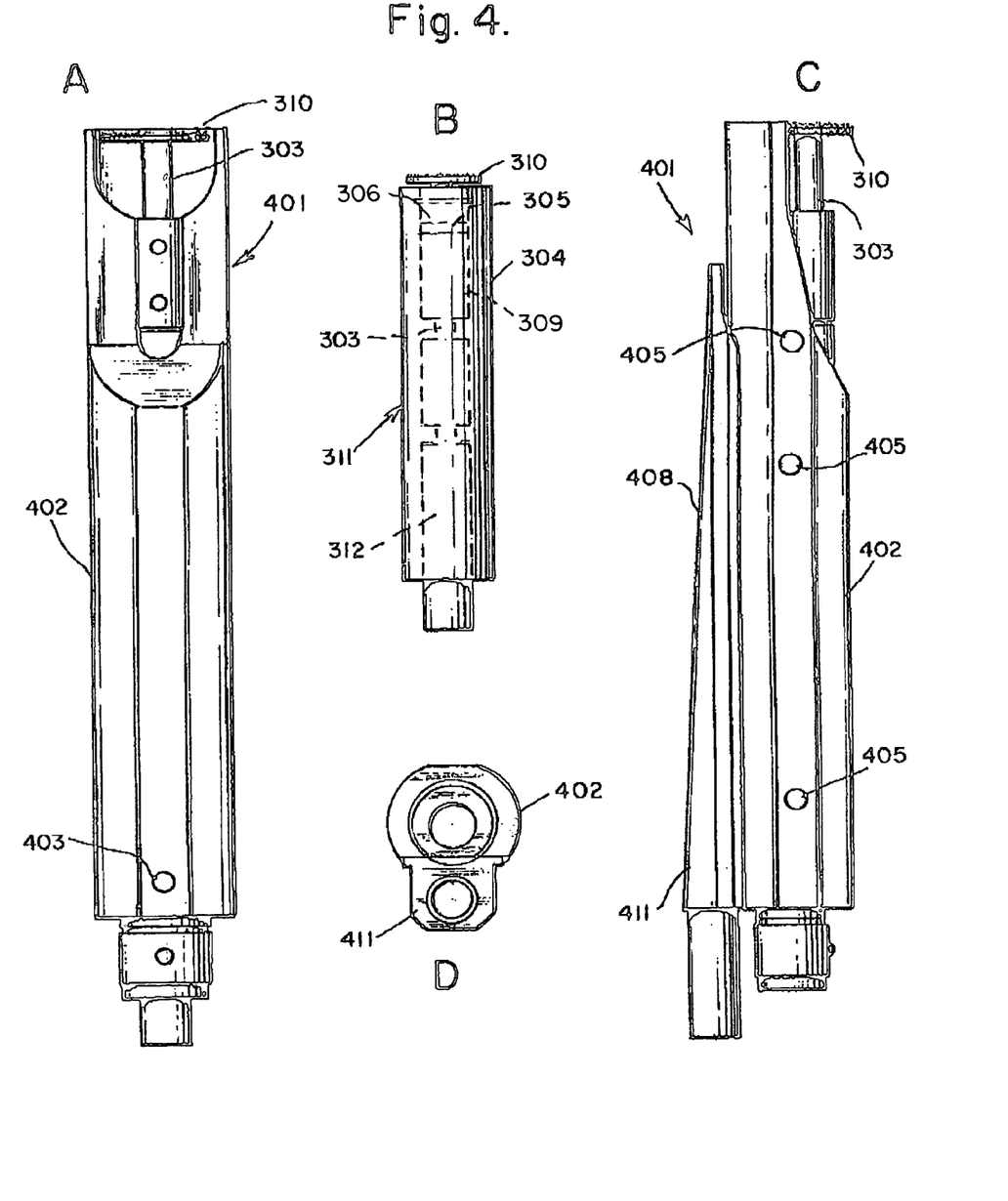

FIG. 4 illustrates a specialized handpiece 402 fabricated according to the teachings of this invention to incorporate a first channel for the support for the shaft 303 of the selected rotating tool, a guard partially encircling the tool mounted on the shaft and a second channel which may be attached to a vacuum source. This arrangement generally designated 401 and is fabricated to directly attach to a preferred motor by means of a flexible shaft. The rotating tool illustrated as mounted in the handpiece 402 is a diamond cutoff disk 310 mounted on the end of shaft 303. In the preferred embodiment, the center of the disk is welded to the shaft rather than attached to a shaft by a screw or bolt. This arrangement creates a flat surface on the topside of the disk and is preferred for polishing, as it does not have any high points. The disk 310 may be used in this arrangement to slice off a portion of a tooth rather than grind off the portion with a cutting surface known as a burr. The partial cutaway view in FIG. 4 B illustrates the end of the shaft 303 remote from the disk 310 to be removably insertable within the bearing support sleeve 304 through the bearing 305. The shaft 303 may be further protected by a hollow brass tube 309. A connector 311 attaches the end of the shaft 303 remote from the disk 310 to an adapter 312 which is adapted to slip directly into the end of a motor driven flexible shaft that compatible with the selected motor obtained under the trademark SUHNER. Another preselected shaped adapter 312 may be mounted to the connector 311 to facilitate easy connection to a flexible shaft compatible with the DREMMEL® motor. A latch 413 may be mounted on the handpiece 402 engagable with a catch formed on the end of the flexible shaft to hold the end of the flexible shaft within the hand piece 402. The illustrated hand piece 402 may be reconfigured by replacing the cut-off disk 310 with a selected burr (cone, cylinder or ball) and used for care and maintenance, particularly in the front portions of the horse's mouth.

A flange 411 may be added to the hand piece 402 to provide room for a second channel that functions as a vacuum channel 408. This second channel is fabricated within the handpiece 402 and flange 411. An orifice 410 of a preselected shape may be fabricated in the handpiece 402 near the cutting surface of the rotating tool 310. The vacuum channel 408 is fabricated to have one end in communication with the orifice 410 and the other end adapted to be connected to a vacuum source. The vacuum channel 408 provides a hollow pathway starting from the orifice 410 for the removal of debris through the second channel upon connection to a vacuum source. Some segment of the second channel for the vacuum path and the first channel for the shaft within the shaft support may be in common before being bifurcated. FIG. 4 D depicts how the flange 411 is held within the handpiece 402 with a snug fitting tongue and groove arrangement 412 and kept in place by a set screw 405. In the preferred embodiment the snug fit eliminates the need for a gasket to maintain sufficient vacuum differential to suck out dust and debris.

Figure 5:
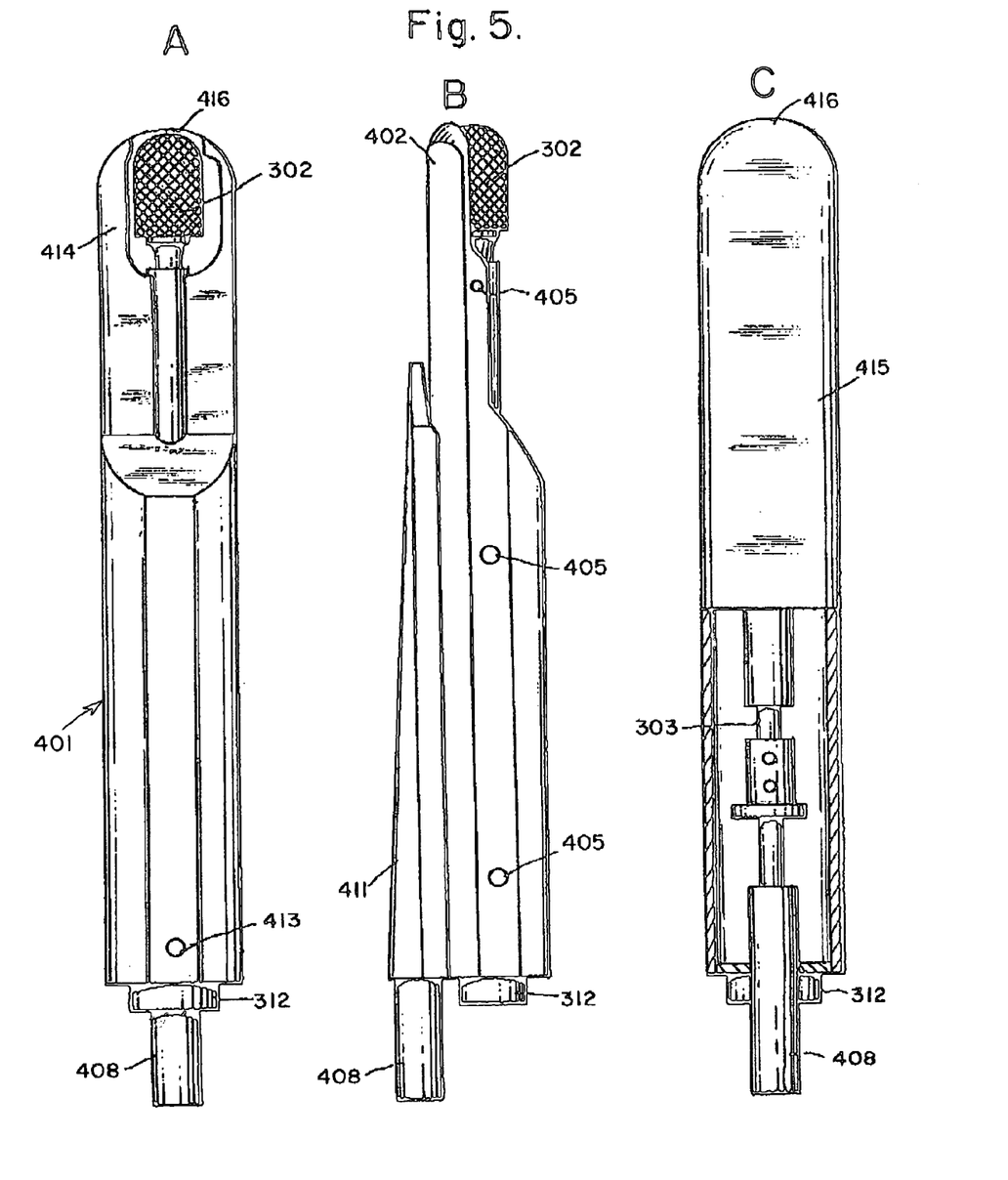

FIG. 5 A, B and C depicts a hand piece generally designated 401 fabricated according to the teachings of this invention. The arrangement illustrated in FIG. 5 A, B and C is shaped and sized for maintenance of the incisor teeth of the horse. The exposed portion of the cutting surface 302 is minimized by fabricating the outer capped top 402 of the handpiece 401 to be close fitting and encircling a large portion of the cutting surface 302. This minimizes the opportunity for the fleshy parts of the horse's mouth to become entangled between the cutting surface 302 and the handpiece 401. The edges 414 of the hand piece 401 below the cutting surface 303 are shaped to provide a smooth slightly curved surface that slips smoothly over the teeth and allows the exposed cutting surface to be forcibly pressed against the selected area of the tooth with minimal, non-interfering contact of the hand piece 401 with the teeth.

Figures 6B, 6F, 8, 9, 10:
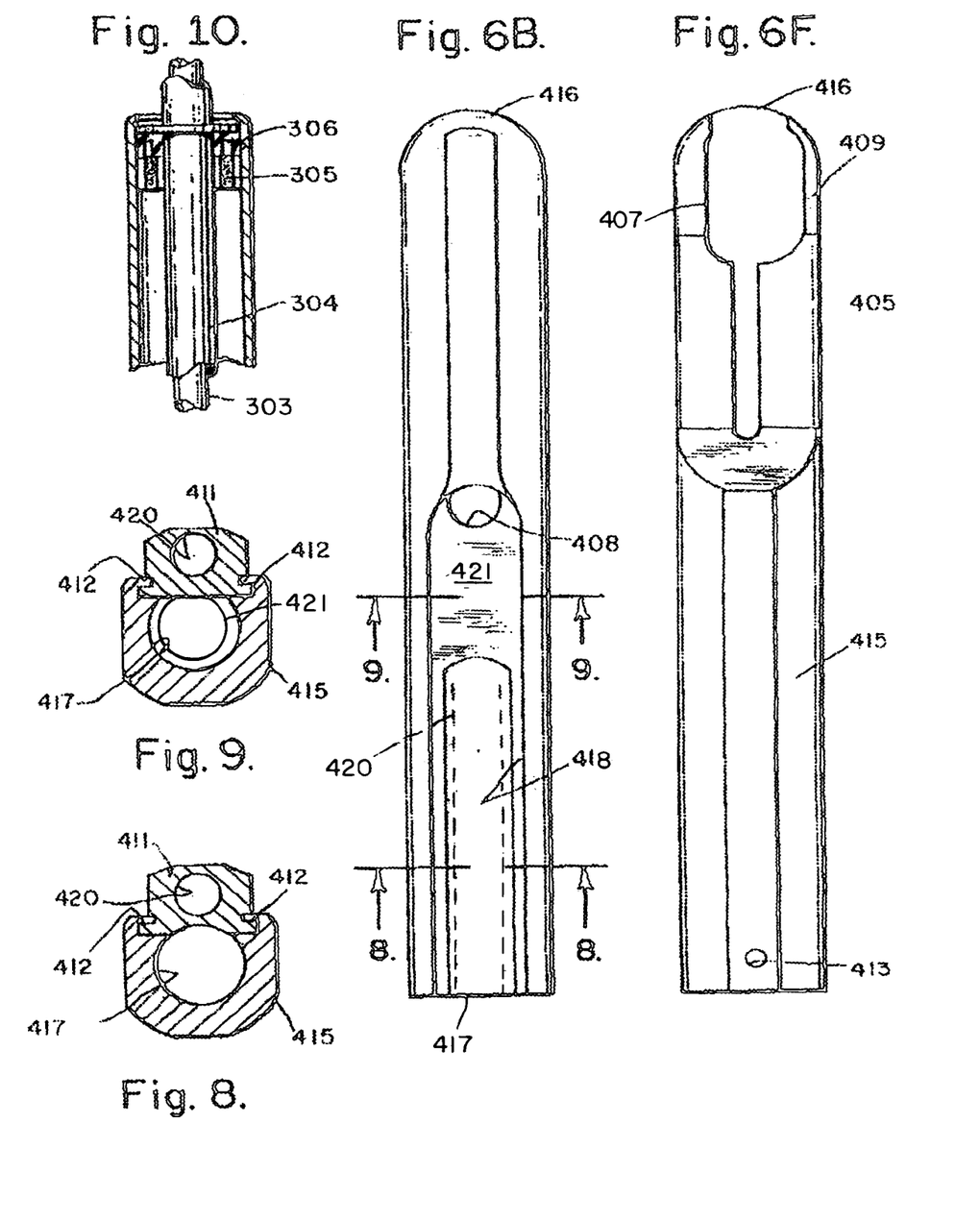
Figure 6H:
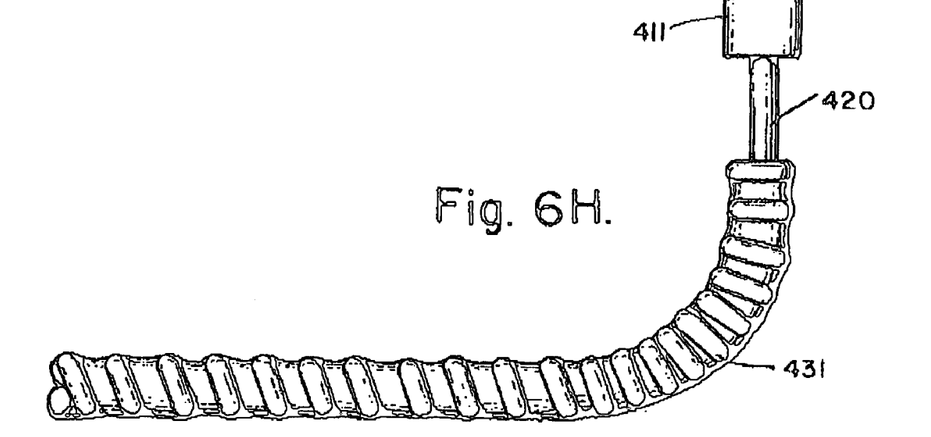
Figure 7B:
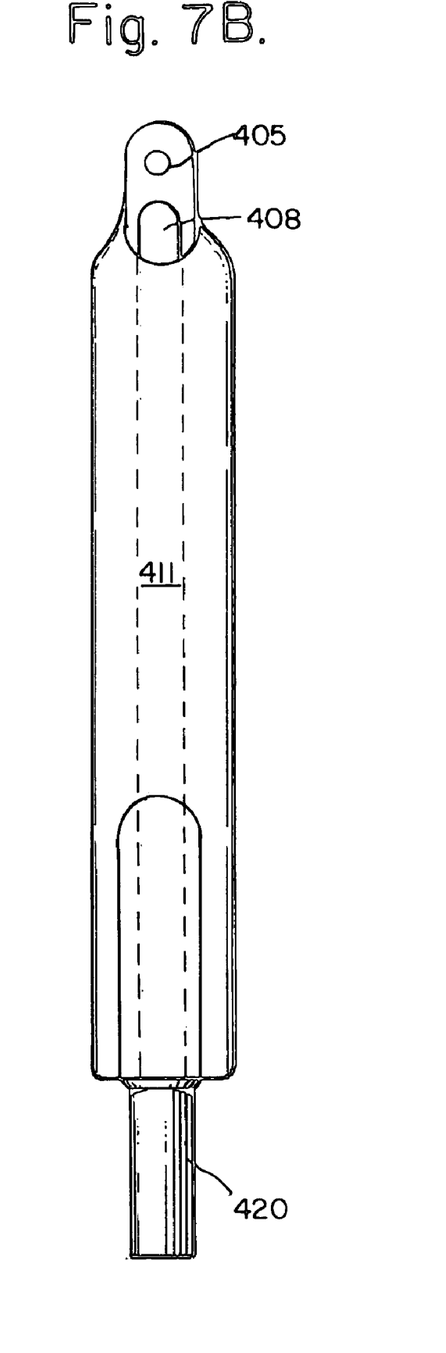
Figure 7F:
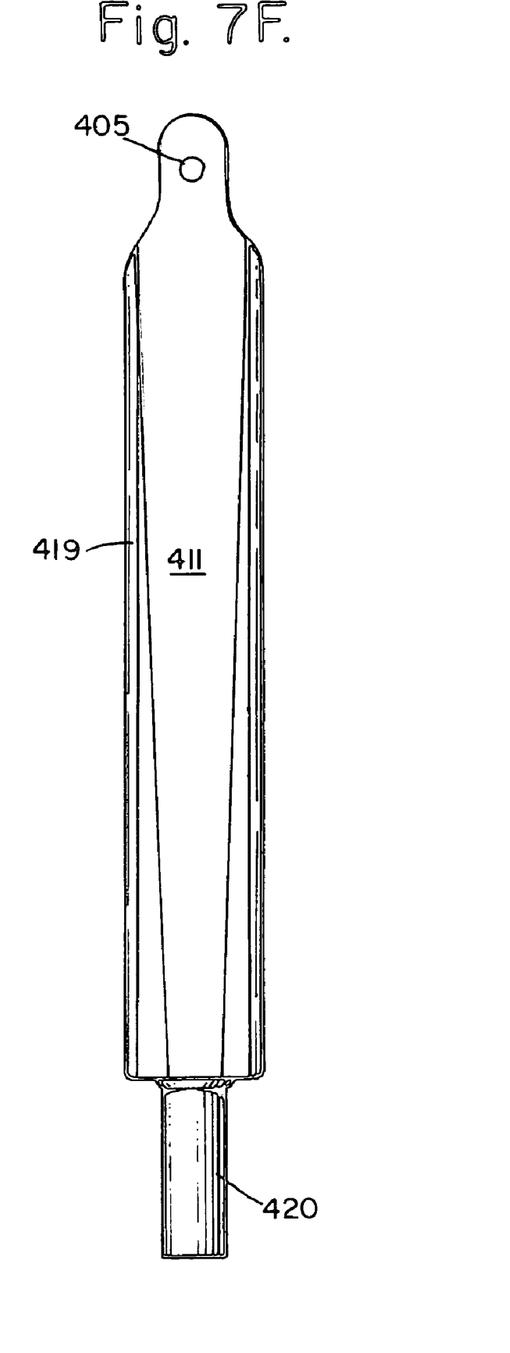

The close fitting of the cutting surface to the handpiece 401 is achieved in the preferred embodiment by fabricating the base 415 of the handpiece 401 as illustrated in FIGS. 6 F and 6 B. In the preferred embodiment, the base 415 is machined of aluminum bar stock to form a rounded cap 416 on one end and access channel 417 open on the other end. Wall 407 is shaped to form an encircling guard around a portion of the cutting surface thereby exposing only a selected portion of the cutting surface near the rounded cap 416. Wall 407 extends away from the rounded cap 416 and toward the access channel 417 to form a first channel for the shaft 303 mounted within the shaft support sleeve 304 as illustrated in FIG. 10. This shaft channel is bifurcated below the exposed cutting surface to communicate with a second channel 408, which is part of the vacuum path. Second wall 409 forms an orifice 410 near the cutting surface. A flange mount 418 is formed as shown in FIG. 6 B as a grooved opening wherein the flange 411 may be mounted. The flange 411 illustrated in FIGS. 7 F and 7 B is a support for a hollow tube 420 one end of the tube 420 communicating with the vacuum channel 408 and the other end extending beyond the flange 411 and attachable to a vacuum source. The edges 419 formed around the periphery of the flange 411 are a shaped as a tongue surface engagable with the groove formed in the periphery of the flange mount 418 making a snug fitting tongue and groove arrangement 412, snug enough to prevent dissipation of the vacuum pressure so as to not decrease the suction of dust and debris from inside the mouth of the horse passing along the path from the orifice 410 through the vacuum channel 408 and hollow tube 420 to the vacuum source, a SHOP VAC.® with appropriate hoses 431 similar to that illustrated in FIG. 6 H. The vacuum hoses 431 which join the end of the hollow tube 420 to the vacuum source may be tied to the powered flexible shaft so that as the user moves the hand piece, the line providing the rotational power and the line providing the vacuum source move with the hand piece as a unit.

A latch 413 may be mounted in the base 415 at a position to engage a catch mounted on the flexible shaft to secure the flexible shaft with the base 415.

FIG. 8 is a cross section of the base 415 with flange 411 mounted therein by the tongue and groove 412.

FIG. 9 is a cross section of the base 415 with flange 411 installed. A third wall forms a bearing support channel 421 starting near this position and extending in the direction of the rounded cap 416 until it intersects with wall 407.

FIG. 10 illustrates a bearing support sleeve 304 with a bearing 305 and upper shaft seal 306 mounted within one end.

To assemble the arrangement, a selected tool comprised of a cutting surface 302 and shaft 303 is inserted through the base 415 starting at guard 407 and then into the bearing support channel 421. The bearing support sleeve 304 is then inserted into the bearing support channel 421 engaging the shaft 303 through the bearing 305 so that the shaft 303 extends beyond the end of the bearing support sleeve 304 remote from the bearing. The bearing support sleeve 304 is secured in place within the bearing support channel 421 by setscrews 405. Now referring to FIG. 5 C, a connector 311 being first mounted to an adapter to a flexible shaft 312, is mounted on the extended end of the shaft 303. The adapter 312 being secured in place by a setscrew 405.

Figure 11:
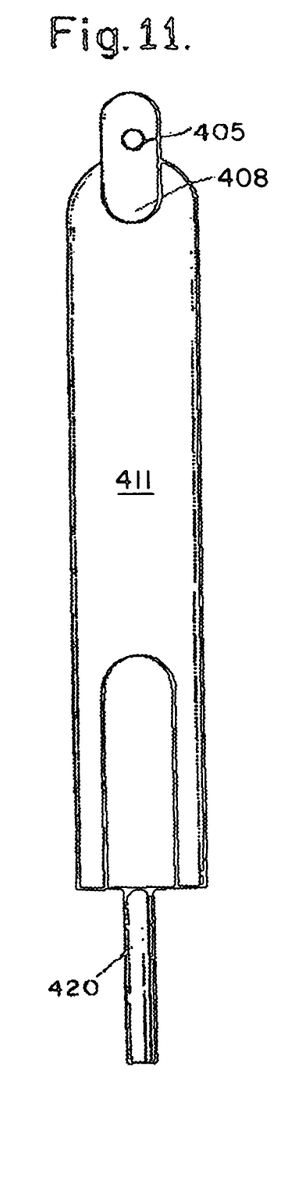
FIGS. 11 and 11F are a view of another embodiment of the present invention, FIG. 11 E is a view of the extended shaft.
Figure 11E:
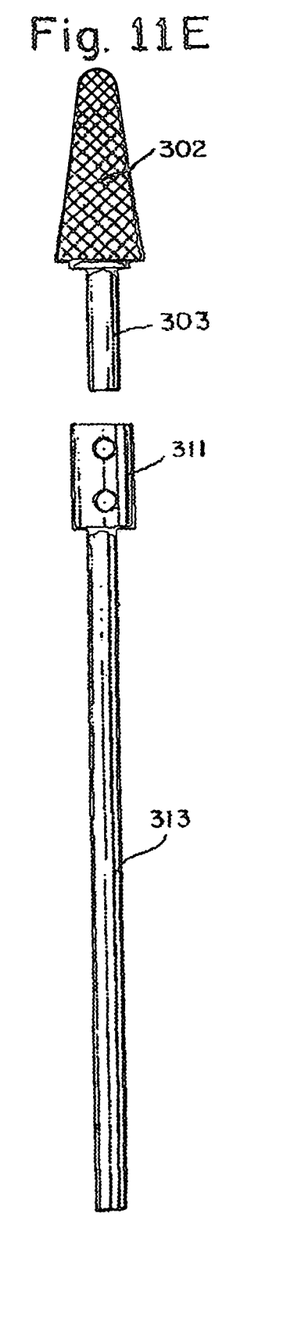
Figure 11F:
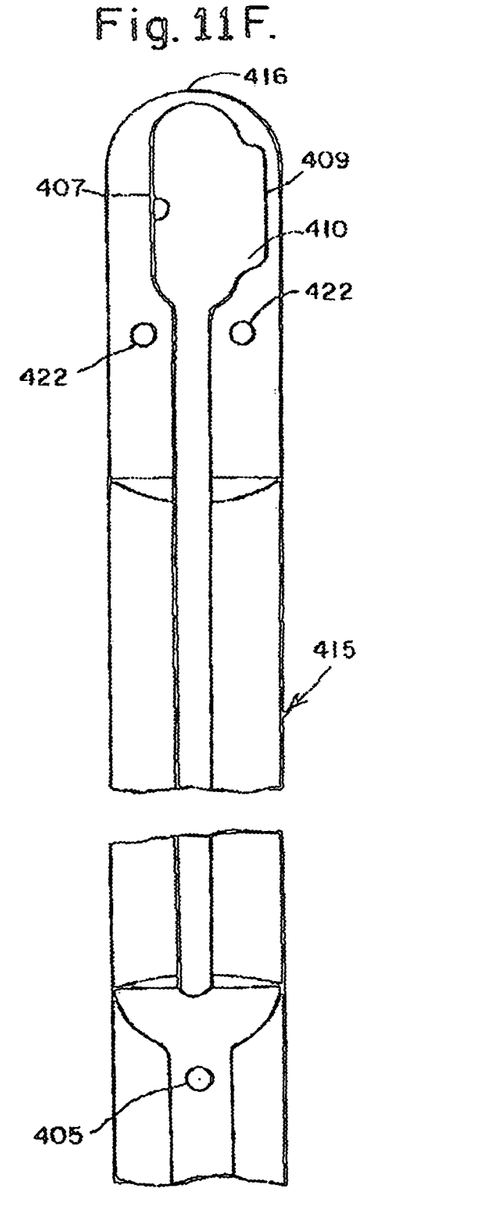

FIG. 11F illustrates the base 415 of an extended arrangement sized for reaching the rear molars inside the horse's mouth and fabricated according to the teaching of the invention. In the preferred arrangement, the base 415 is 14 inches long. This additional length requires the shaft 303 attached to the cutting surface 302, the bearing support sleeve 304, flange 411, and hollow tube 420 illustrated in FIG. 11, to also be proportionally longer. These items may be extended as illustrated in FIG. 11 E. A connector 311 attaches shaft extension 313 to the shaft 303 of the cone shaped cutting surface 302.

An additional setscrew 405 may be used to secure the longer bearing support sleeve 304. The orifice 410 formed by wall 409 at the front end of the vacuum channel 408 remains similar as it is sized in relationship to the cutting surface 302.

Figure 12:
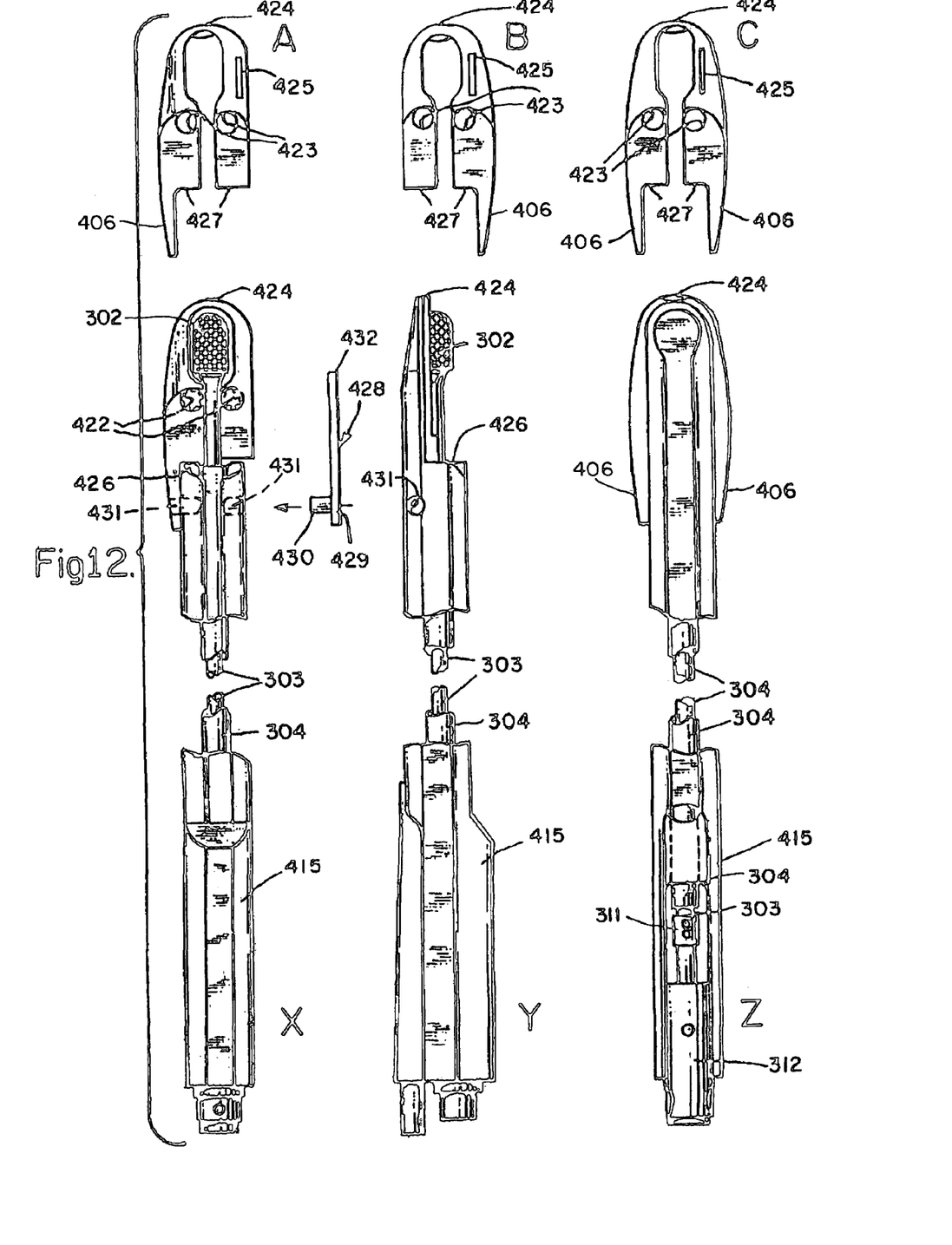

FIGS. 12 X, Y and Z illustrate the assembled extended arrangement having a base 415 approximately 14 inches long supporting a rotary tool having a cutting surface 302 and shaft 303 mounted within a bearing support sleeve 304. A connector 311 with adapter to flexible shaft 312 is mounted on the end of the shaft 303 remote from the cutting surface 302.

Because the back of the horse mouth is surrounded by fleshy material, the rounded cap 416 of the base 415 may provide inadequate separation between the cutting surface 302 and the fleshy material. An external guard 406 may be mounted on the base 415 to enhance the separation of the fleshy material from the cutting surface 302. Posts 422 are mounted near the cutting surface 302. FIGS. 12 A, B and C illustrate three shapes, left, right and balanced, respectively of a type of extended guard 406 which may be removably attached to the base 415 to provide extra separation between the fleshy material and the cutting surface 302. Each extended guard 406 is fabricated with walls 423 forming holes engagable with the posts 422. Wall 424 forms an opening to expose the cutting surface 302 and wall 425 forms an opening communicating with the orifice 410. Wall 426 forms a shallow channel in the base 415 into which the lower edge 427 of the extended guard 406 may be inserted. Wall 431 forms a retaining hole in each side of the base 415. A wedge arrangement 428 having an offset head 429 and a pin 430 is insertably removable by pin 430 into a selected retaining hole 431 whereby the wedge arrangement 428 is rotated by handle 432 to a position wedging the extended guard 406 securely into place by means of the offset head 429.

Figures 13, 14, 15:
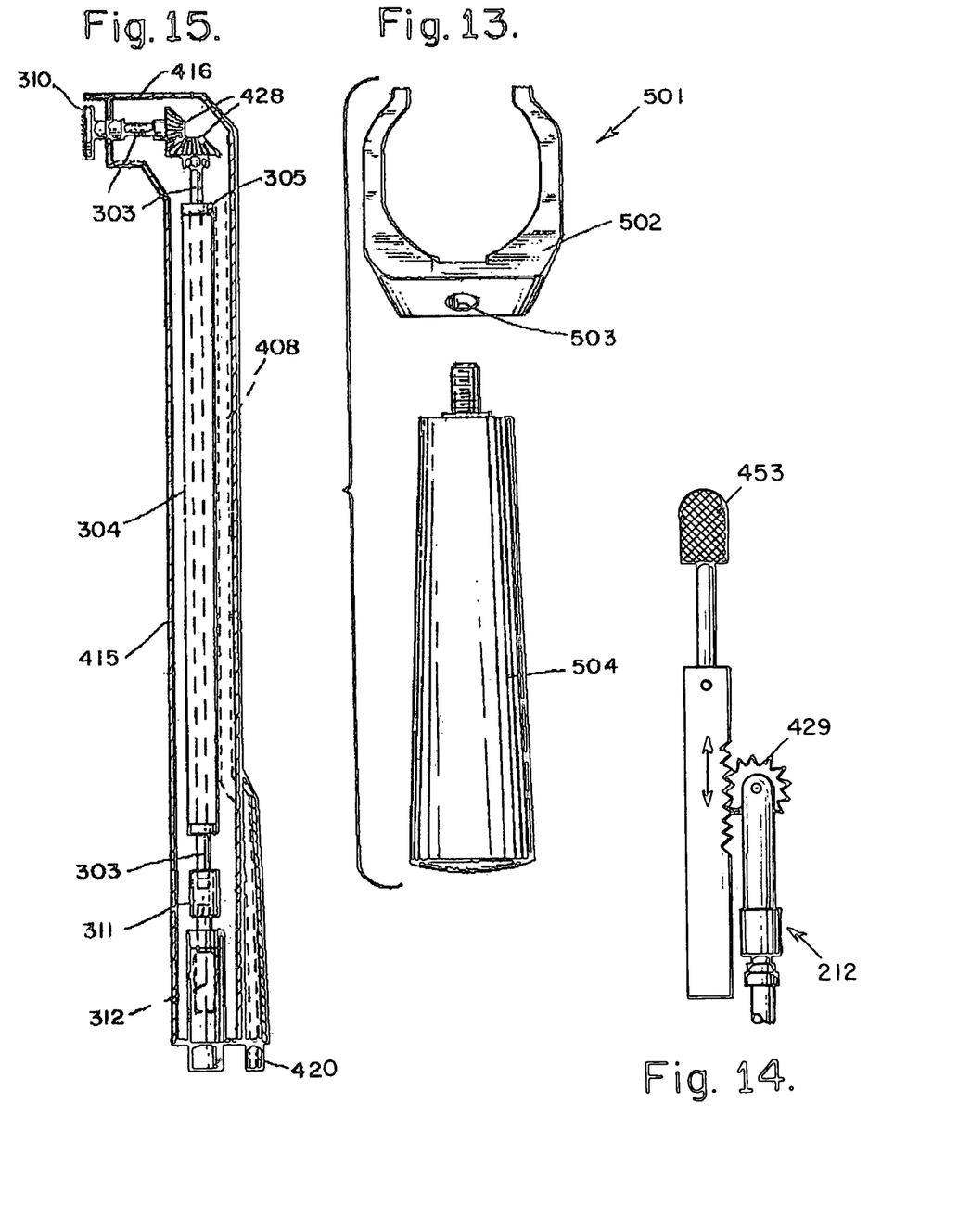
FIG. 13 is a view of an attachable handle.
FIG. 14 is a view of another embodiment of the present invention.
FIG. 15 is a detailed view of another embodiment of the present invention.

An attachable handle generally designated 501 is illustrated by FIG. 13. This handle may be mounted on the remote end of the 14 inch base 415 like a pistol grip to provide a leveraged advantage especially for inserting and guiding the extended arrangement assembled to the rear molars for removing tooth material. This handle incorporates a clamp 502 removably mountable over the end of the base 415 to a position remote from the cap 416. Walls 503 form a threaded hole in the clamp 502 that accepts an extended screw 504 which upon being threaded into threaded hole 503 secures the handle 501 in place as well as preventing movement of clamp 502.

Other arrangements that are especially useful for the care of the rear molars is illustrated in FIG. 15, the base 415 providing support for the shaft 303 within bearing support sleeve 304, all similar to the above embodiments but a set of gears 428 are mounted on the shaft 303 to change the profile of the shaft 303 by ninety degrees. This embodiment is particularly useful with the cut-off disk 310 mounted therein in a position which is essentially horizontal. The cut-off disk can be easily positioned to score a portion of a tooth to be chipped off or used to polish and smooth selected teeth even in the rear portions of the horse's mouth.

The arrangement illustrated in FIG. 14 is fabricated according to the above teaching but incorporates a set of gears 429 mounted within the base 415. The gears 429 are adapted to change the rotational motion of the shaft 303 to a reciprocating motion. In the preferred embodiment, the reciprocating motion is approximately ¼ inch back and forth. A tool pad 453 is removably attachable to a reciprocating tool handle. The tool pad 453 has a flat cutting surface and is particularly useful for the care and maintenance of the rear most molars in the horse's mouth. The hand piece 415 may be pistol shaped to supply leverage and to provide adequate mounting for the set of gears 428 within the hand piece 415 at a point that is not inserted into the mouth of the horse.

The units in the preferred embodiment are fabricated of a preselected material such as aluminum, chosen to be lightweight, strong, easily machined and able to function in a wet environment. The surface of the aluminum may be anodized to protect the material from corrosion. A lightweight urethane material is preferred for the slip on extended guard 406 shown in FIG. 1 C.

Figure 16:
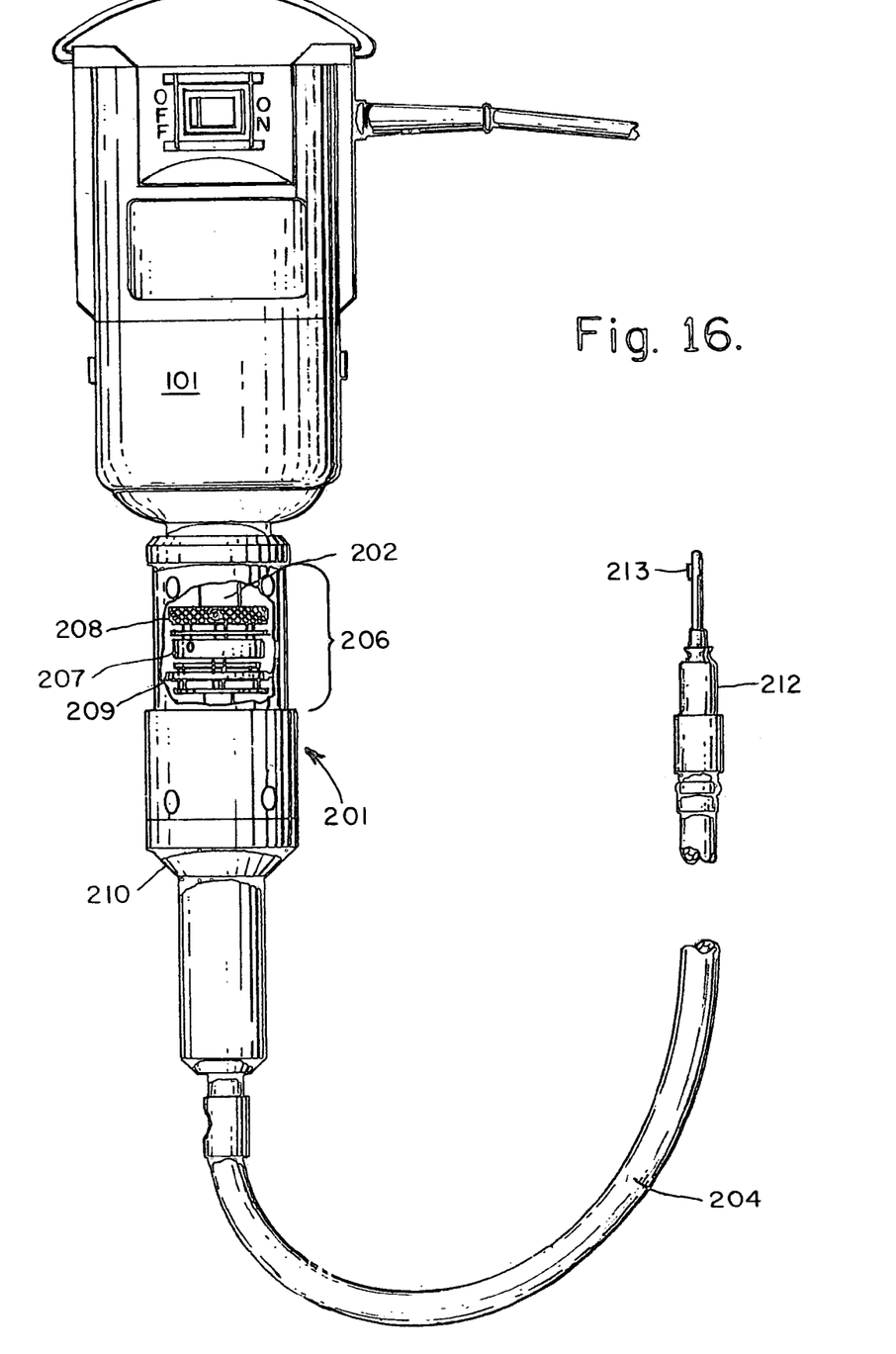
FIG. 16 is a schematic of the power train.

FIG. 16 is a schematic representation of the power train generally designated 201. The basic configuration is a selected motor 101. The tools may be mounted directly onto the shaft of the motor 101 or separated from the motor 101 by a flexible shaft 204 as discussed above. Both configurations provide a direct connection between the motor 101 and the cutting surface 302 of the tool. In the preferred embodiment of the power train 201, an adjustable torque clutch 206 is included. Should the preselected torque of the clutch 206 be exceeded during use of the arrangement fabricated according to the teachings of this invention, the clutch 206 will disengage the powered motion of the motor 101 from the tool thereby minimizing possible injury to the horse or user and allow the user to safely clear any obstruction of the arrangement before continuing use.

Figure 17:
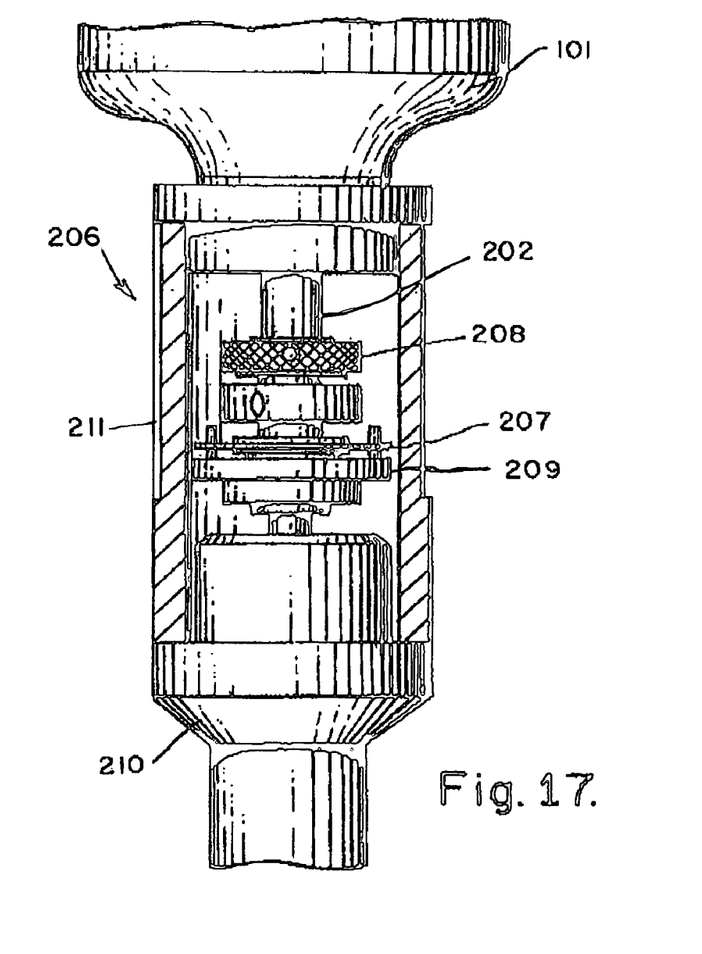
FIG. 17 is a view of the clutch arrangement.

FIG. 17 illustrates a clutch 206 having a set of clutch plates 207, a torque adjustment knob 208 that sets the tension between the clutch plates 207. An end adapter 209 compatible with the flexible shaft 204 is mounted on the clutch 206 remote from the motor 101. The clutch 206 is mounted within the collet 202 of the motor 101.

A clutch housing 210 is fabricated to slip over the clutch 206 and onto the motor 101 to a position whereby the end adapter 209 is engagable by the end of the flexible shaft 204 which is mounted within the clutch housing 210. A sliding window 211 may be mounted on the clutch housing 210 to allow easy access by the user to the torque adjustment knob 208.

FIG. 16 illustrates a collar 212 fabricated from stainless steel and mounted on the flexible shaft 204 remote from the end of the flexible shaft mounted to the clutch housing 210. The collar 212 is fabricated with a catch 213 engagable by the latch 413 mounted on the base 415 of the hand piece 401 when the collar 212 is inserted within access channel 417. The rotational motion of the motor 101 is selectively, interruptably transmitted to the clutch 206, through the flexible shaft 204 engagable with the flexible shaft adapter 312 to the cutting surface 302.

Since certain change may be made in the above apparatus without departing from the scope of the invention herein involved, it is intended that all matter contained in the above description, as shown in the accompanying drawing, shall be interpreted in an illustrative, and not a limiting sense.

What is claimed is:

1. An arrangement of a tool insertable into the mouth of a house for the care and maintenance of teeth while providing protection of soft tissue within the mouth of the horse and comprising in combination:
  an electric rotary motor having a means to hold said tool along the axis of rotation of said motor, said tool having a tooth cutting surface of a preselected size and shape;
  a shaft having one end mounted to said cutting surface and the other end attachable to said motor holding means thereby supplying rotational motion to said tool;
  a shaft support having a bearing mounted at a preselected position within said shaft support means and a bearing seal mounted at a position between said bearing and said cutting surface through which said shaft may be inserted and supported for rotary motion without binding;
  a hand piece having a channel through which said shaft support means is removably insertable; and,
  a cutting surface guard fabricated as a portion of said hand piece and shaped to be in encircling relation about a selected portion of said cutting surface thereby exposing only a portion of said cutting surface under the condition of said shaft support means, having said shaft inserted therein, is mounted within said shaft support channel of said hand piece and said shaft engaged within said holding means thereby allowing a user of the arrangement to guide said hand piece containing the partially guarded tool into the mouth of the horse to separate said soft tissue from a preselected portion of a tooth with said cutting surface guard and position the unguarded portion of said cutting surface against a tooth to remove a selection portion of said tooth by means of said tool in rotary motion.

2. The arrangement defined in claim 1 further comprising a brass sleeve mountable around said shaft under the condition of said shaft being inserted through said bearing and bearing seal into said shaft support means, said brass sleeve providing separation between said shaft and said shaft support means.

3. The arrangement in claim 1 wherein said shaft support means further comprises gearing means mounted within said shaft support means and in communication with said shaft to change the rotational motion of said shaft attached to said motor holding means into reciprocating motion which may be applied to said cutting surface mounted on said shaft remote from said gearing means.

4. The arrangement in claim 1 wherein said shaft support means further comprises gearing means mounted within said shaft support means and in communication with said shaft to change the profile of the shaft by a preselected angle thereby increasing the range of placement of said cutting surface of said tool.

5. An arrangement of a tool insertable into the mouth of a house for the care and maintenance of teeth while providing protection of soft tissue within the mouth of the horse and comprising in combination:
  an electric rotary motor having a means to hold said tool along the axis of rotation of said motor, said tool having a tooth cutting surface of a preselected size and shape;
  a shaft having one end mounted to said cutting surface and the other end attachable to said motor holding means thereby supplying rotational motion to said tool;
  a shaft support means having a bearing mounted at a preselected position within said shaft support means and a bearing seal mounted at a position between said bearing and said cutting surface through which said shaft may be inserted and supported for rotary motion without binding;
  a hand piece having a channel through which said shaft support means is removably insertable; and,
  a cutting surface guard fabricated as a portion of said hand piece and shaped to be in encircling relation about a selected portion of said cutting surface thereby exposing only a portion of said cutting surface under the condition of said shaft support means, having said shaft inserted therein, is mounted within said shaft support channel of said hand piece and said shaft engaged within said holding means thereby allowing a user of the arrangement to guide said hand piece containing the partially guarded tool into the mouth of the horse to separate said soft tissue from a preselected portion of a tooth with said cutting surface guard and position the unguarded portion of said cutting surface against a tooth to remove a selection portion of said tooth by means of said tool in rotary motion;

a flexible shaft having one end adaptively mountable to said motor thereby supplying rotational motion to said flexible shaft and the other end having a means to hold said tool along the axis of rotation of the flexible shaft thereby separating said motor from said tool so that said motor may be supported at a position remote from said tool;

a clutch mounted with one end in communication with said motor and another end remote from said motor in communicated with said flexible shaft thereby providing interruptible transmission of motion from said motor to said cutting surface in communication with said flexible shaft said clutch further comprises means to adjust the threshold of torque at which said motion is interrupted.

6. The arrangement in claim 5 further comprising a clutch housing mountable to said motor thereby enclosing said clutch and having a mounting to retain one end of said flexible shaft in communication with said clutch, said clutch housing having an means for access by the user to the means to adjust the torque.

7. An electric motor powered arrangement insertable into the mouth of a horse for the care and maintenance of equine teeth while providing protection of soft tissue within the mouth of the horse and comprising in combination:

a tool having a tooth material removal surface;

a shaft having a first end mounted to said tool and a second end attachable to said electric motor whereby said tooth material removal surface has a powered motion;

a hand piece fabricated with an internal shaft channel;

a bearing support sleeve;

at least one bearing mounted within said support sleeve at a preselected position whereby said bearing accepts the insertion of said shaft through said bearing thereby exposing the end of said shaft remote from said tooth removal surface, said bearing support sleeve mounted with said internal shaft channel whereby said exposed end of said shaft is attachable to said electric motor, said bearing providing support for said shaft under the condition of said tooth material removal surface tool being guided into contact with a preselected tooth and pressed against the tooth until a preselected portion of the tooth is removed while said tooth material removal surface is under powered motion;

a protective shield fabricated as part of said hand piece at a preselected position and shaped to expose a preselected portion of said tooth material removal surface of said tool retained within said hand piece, said exposed portion guided into contact with a preselected portion of the tooth whereby the remaining non-exposed surface is separated from other portions of the horses mouth including said soft tissue; and, a sleeve mountable over said shaft within said shaft hand piece whereby said sleeve provides additional bearing means between said shaft and said hand piece without binding.

8. The arrangement defined in claim 7 wherein said bearing support sleeve means further comprises a bearing mounted at a preselected position within said bearing support sleeve and a bearing seal mounted at a position between said bearing and said cutting surface through which said shaft may be inserted and supported for rotary motion without binding.

9. The arrangement defined in claim 7 further comprising a flexible shaft having one end adaptively mountable to said motor thereby supplying rotational motion to said flexible shaft and the other end having a means to hold said tool along the axis of rotation of the flexible shaft thereby separating said motor from said tool so that said motor may be supported at a position remote from said tool.

10. The arrangement defined in claim 7 further comprising preselected sized and shaped extended guards mountable to said cutting surface guard to provide additional separation between said cutting surface and said soft tissue within the mouth of the horse.

11. The arrangement defined in claim 10 wherein said extended guard further comprises an orifice formed near said cutting surface and a vacuum channel one end of which is in communication with said orifice, the other end of said vacuum channel adapted to be removably attachable to a vacuum source whereby the dust and debris created by the removal of a selected portion of a tooth may first enter said orifice and then said channel to be sucked out of the mouth of the horse and deposited into said vacuum source.

12. The arrangement in claim 7 wherein said bearing support sleeve further comprises gearing means mounted within said bearing support sleeve and in communication with said shaft to change the rotational motion of said shaft attached to said motor holding means into reciprocating motion which may be applied to said cutting surface mounted on said shaft remote from said gearing means.

13. The arrangement in claim 7 wherein said bearing support sleeve further comprises gearing means mounted within said bearing support sleeve and in communication with said shaft to change the profile of the shaft by a preselected angle thereby increasing the range of placement of said cutting surface of said tool.

14. The arrangement in claim 9 wherein said adaptive mounting of said flexible shaft is to a motor owned by the user.

15. The arrangement in claim 9 wherein said means to hold said tool is a handle owned by the user, said flexible shaft having means to adaptively mount said handle on the end of said flexible shaft under the condition of said shaft mounted within said handle.

16. The arrangement in claim 9 further comprising a clutch mounted with one end in communication with said motor and another end remote from said motor in communicated with said flexible shaft thereby providing interruptible transmission of motion from said motor to said cutting surface in communication with said flexible shaft.

17. The arrangement in claim 16 wherein said clutch further comprises means to adjust the threshold of torque at which said motion is interrupted.

18. The arrangement in claim 17 further comprising a clutch housing mountable to said motor thereby enclosing said clutch and having a mounting to retain one end of said flexible shaft in communication with said clutch, said clutch housing having an means for access by the user to the means to adjust the torque.

19. The arrangement in claim 7 wherein said hand piece and guard are fabricated from aluminum.

20. The arrangement in claim 19 wherein the exposed surfaces of said aluminum are anodized.

* * * * *